United States Patent [19]

Berger

[11] Patent Number: 4,997,382
[45] Date of Patent: Mar. 5, 1991

[54] PROSTHESIS HANDLING SYSTEM

[76] Inventor: Robert P. Berger, 4421 Rochelle Pl., Encino, Calif. 91316

[21] Appl. No.: 8,064

[22] Filed: Jan. 12, 1987

Related U.S. Application Data

[63] Continuation of Ser. No. 625,302, Jun. 27, 1984, abandoned.

[51] Int. Cl.⁵ .............................................. A61C 3/00
[52] U.S. Cl. .................................... 433/163; 433/223
[58] Field of Search ................. 433/218, 223, 203.1, 433/202.1, 163

[56] References Cited

U.S. PATENT DOCUMENTS

| | | | |
|---|---|---|---|
| 2,219,058 | 10/1940 | Streim | 433/223 |
| 2,318,402 | 5/1943 | Karlstrom | 433/213 |
| 2,793,436 | 5/1957 | Gotlib | 433/203.1 |
| 3,004,343 | 10/1961 | Rydin | 433/203.1 |
| 3,058,216 | 10/1962 | Cohen | 433/223 |
| 3,748,741 | 7/1973 | Yerkes, Jr. | 433/203.1 |
| 4,038,753 | 8/1977 | Klein | 433/11 |

*Primary Examiner*—Cary E. Stone
*Attorney, Agent, or Firm*—Allan M. Shapiro

[57] ABSTRACT

Handle is formed with the metal portion of a dental prosthesis so that the handle can be used for supporting and handling the metal structure from the mold to the final finishing, when the handle is cut off. The handle preferably has both a ring for supporting the structure on a post and a ball for grasping of the metal structure.

6 Claims, 1 Drawing Sheet

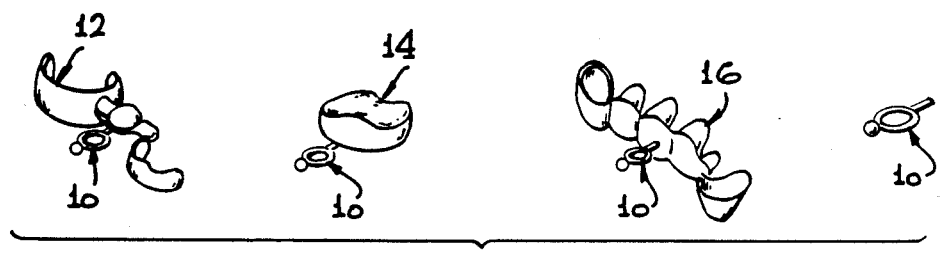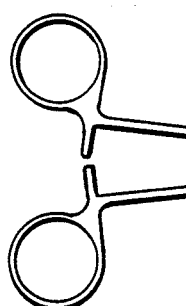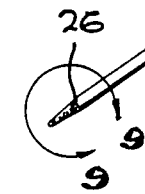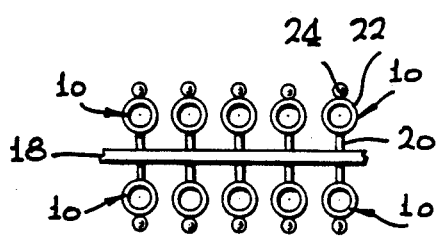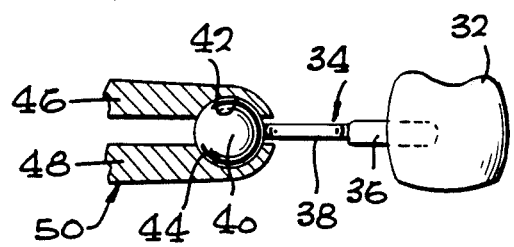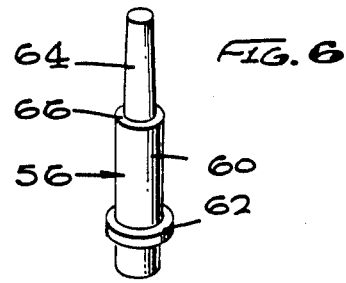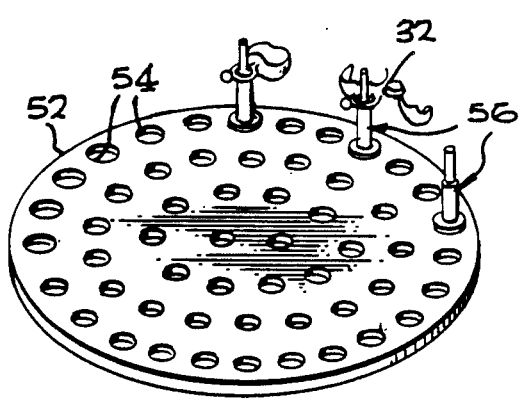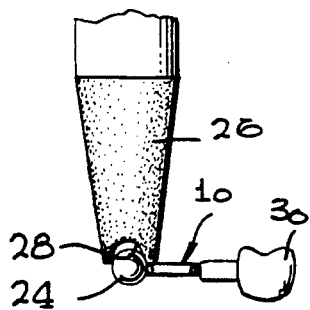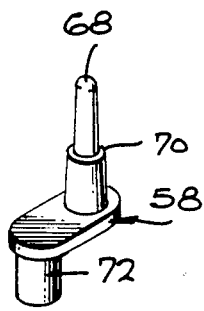

4,997,382

PROSTHESIS HANDLING SYSTEM

This is a continuation application of Ser. No. 625,302 filed June 27, 1984, now abandoned.

BACKGROUND OF THE INVENTION

This invention is directed to a handling system, and particularly a system for handling the metallic portion of a dental prosthesis from the molding of the metal portion, through to intermediate and finishing work on the metal structure, until the cutting off of the handle as the last step.

Dental prostheses are often partially or completely cast of metal in an investment casting lost wax molding process. These prostheses must be handled through the intermediate and finishing processes subsequent to the molding. In some cases, a metallic substructure is cast of metal, and subsequent thereto a ceramic is selectively placed thereon. When suitably positioned and configured, the ceramic is baked on the substructure. In order for the ceramic to properly adhere to the substructure, the metallic substructure must be absolutely clean. Handling such a substructure with the fingers places skin oils thereon, which prevents proper ceramic adhesion. The handling of such a substructure even with gloves can cause contamination of the surface and subsequent poor adhesion. The ideal clean surface is the untouched surface as it comes from the investment casting mold. Cleanliness and convenience in handling are also necessary or helpful in the handling of other dental prosthetic devices. In the past, there has been no handling system by which such can be accomplished.

SUMMARY OF THE INVENTION

In order to aid in the understanding of this invention, it can be stated in essentially summary form that it is directed to a prosthesis handling system wherein a handle is secured to the prosthesis structure, with the handle having supporting means thereon which can be engaged for supporting the prosthesis during the intermediate steps from investment casting to the final finishing step.

It is, thus, an object and advantage of this invention to provide a dental prosthesis handling system wherein a handle is attached to the investment cast portion of the prosthesis and the handle can be engaged to support the investment cast metal structure during intermediate processing.

It is a further object to provide such a handling system wherein the handle is configured to support the metal structure selectively on a support post or by means of a hand tool so that the cast metal structure can be appropriately supported for the work being done thereon.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a perspective view of several different prostheses either in wax form or in cast form showing the handle attached to the dental prostheses and also showing the handle alone, for use in the prostheses handling system of this invention.

FIG. 2 shows a special clamp hand tool used for engaging a portion of the handle, for use in handling the investment cast metal prosthesis structure.

FIG. 3 is an enlarged view, with parts broken away and parts taken in section, showing the engagement of the hand tool on a portion of the handle.

FIG. 4 shows a group of the handles in wax form, whereby one or more of the handles can be removed from the group and attached to the wax master prosthesis for use in molding.

FIG. 5 shows a firing tray with a plurality of posts thereon for the support of prostheses in one step of the prosthesis handling system of this invention.

FIG. 6 is an enlarged view of one of the support pins shown in FIG. 5.

FIG. 7 is an enlarged view of an alternate support pin which can be used in conjunction with a firing tray or another tray.

FIG. 8 is a perspective view of an instrument for manipulating the handle when it is in wax form.

FIG. 9 is an enlarged view, with parts broken away, showing the instrument of FIG. 8 manipulating a wax handle and holding it for attachment to another wax structure.

DESCRIPTION OF THE PREFERRED EMBODIMENT

In FIG. 1, dental prostheses 12, 14 and 16 have attached thereto a handle 10 which is an essential portion of the prosthesis handling system of this invention. In the manufacture of the prosthesis, a wax master is provided, and the wax master is employed to provide a cavity in the molding material in the investment casting lost wax molding process. After the molding material is hardened, the wax is melted out and metal is poured therein. This metal may be a substructure which will receive a ceramic coating over a portion thereof, or may be a metal structure such as a crown. During the processing of the metal structure or substructure cast in the investment mold, the handle 10 is employed to support the metal structure during the intermediate processing from the investment casting step to the final finishing step where the handle is removed.

FIG. 4 shows a plurality of the handles 10, each identical to the other, on a common bar 18. The entire structure in FIG. 4 is of wax. Each handle has a neck 20, ring 22 and sphere 24. Stick 24, see FIGS. 8 and 9, has a resilient nose piece 26 which is formed with resilient jaw opening 28. The jaw opening is engaged over the ball 22 of one of the wax handles 10 and the stick is used to bring the wax handle 10 adjacent a wax master prosthesis 30, see FIG. 9. The wax handle 10 is attached to the prosthesis by the application of limited heat so that it is adjoined as generally indicated in FIG. 1. For a long prosthesis with a substantial metal structure or substructure spanning several tooth widths, two or more handles 10 can be attached. As is seen in FIG. 9, the jaw opening 28 of the soft nose piece 26 grasps ball 24. Even though ball 24 is a wax structure at this point, the jaw opening 28 can hold and control handle 10 to hold it in position for attachment as shown in FIG. 9.

The wax master of the prosthesis, including handle 10, is completed, attached to appropriate sprue and gates, and is placed in a mold for investment casting. The molding compound is poured around the wax master and, after the molding compound is hardened, the wax master is melted out. Next, metal is poured into the mold cavity to form a metal structure of a prosthesis or a metal substructure of a ceramo-metal prosthesis.

The prosthesis handling system of this invention is particularly useful in the handling of the metal substructure which is to become a part of a ceramo-metal prosthesis. The surface of the substructure must be clean for the ceramic to bond to the investment cast metallic substructure. This precludes handling of the metallic substructure, even handling by gloves. If conventional tools are used in handling such a substructure, the serrated jaws of the conventional tools can cause damage to critical surfaces. However, in accordance with this invention, the investment cast metal structure carries thereon the handle 10 in metallic form. It has been investment cast into metal, along with the rest of the metal structure. FIGS. 2 and 3 illustrate prosthesis 32, which is an investment cast metallic prosthesis or prosthesis substructure and compares with the wax master prosthesis 30 shown in FIG. 9. The metal prosthesis substructure 32 carries thereon metal handle 34, which is the same as metal handle 10. Metal handle 34 has a neck 36, ring 38 and ball 40. As is seen in FIG. 3, the ball 40 is substantially spherical and is grasped within the cavities 42 and 44 respectively in jaws 46 and 48 in instrument 50. Instrument 50 is similar in structure to the conventional surgical clamp, but instead of having serrated jaws, has the cavities 42 and 44 adjacent the tip thereof. The cavities 42 and 44 are preferably shaped so that they are part of the surface of the sphere of the same diameter as ball 40. Thus, the ball 40 can be clamped therein. When clamped in that manner, the instrument 50 can be used as a manual support for the handle 34 and the metal prosthesis structure 32 which is cast with the handle. Thus, the metal prosthesis can be engaged, supported, positioned and moved through the manual control of instrument 50 without touching any of the surfaces on the metal structure 32 which will require work prior to finishing. Thus, the other surfaces of the metal prosthesis are unmarked and uncontaminated by touching.

It is particularly important to note that the jaws of instrument 50 do not extend past the ring 38. In this way, the entire opening in the ring is available when the substructure is being handled by instrument 50 so that the ring may be placed over support pins of the type shown in FIGS. 5, 6 and 7. In this way, a prosthesis can be handled without manual or instrument engagement on the prosthesis metal structure or substructure from the moment it is divested from the mold to the final removal of the handle.

Particularly in the case of a metal substructure of a ceramo-metal prosthesis, the substructure must be supported during the placement thereon of the ceramic material and must be supported during firing of the ceramic material. FIG. 5 shows firing tray 52, preferably of ceramic structure and capable of withstanding firing heat. Firing tray 52 has a plurality of openings 54 therein with the openings extending generally upright with respect to the plane of the firing tray. Supporting pins 56 and 58, respectively shown in FIGS. 6 and 7, can be inserted into selected openings 54 to carry thereon the substructure for firing. Pin 56 has a body 60 which carries a stop 62 in the form of a circular ring. The lower part of the body inserts into the opening 54 and stop 62 engages against the top surface of tray 52. Tapered pin 64 ends in shoulder 66 which is the top of body 60. The entire structure is of a suitable material to withstand firing temperatures. Tapered pin 64 and shoulder 66 are dimensioned so that ring 38 can be received thereover, with the ring engaging against shoulder 66. In this way, the metal substructure, carrying its ceramic coat, can be positioned upon the tray, as shown in FIG. 5. The entire tray carrying several of such substructures is placed in the furnace for firing of the ceramic. To aid in spacing of the various substructures on tray 52, the support pin 58 is provided. Support pin 58 is the same as support pin 56 except that tapered pin 68 and shoulder 70 are offset from the lower part of the body 72 so that the support pin can be offset from the openings 54 in the firing tray. In this way, infinite adjustment between adjacent tapered pins 68 is possible. This is particularly useful when there are two handles 34 on a metallic substructure which is to be fired.

After firing, the ceramic is hard and, if no further ceramic work is contemplated, the ceramo-metallic prosthesis can be handled by gloves. As part of the final finishing of the prosthesis, the handle 34 is cut off and the place where the neck 38 was attached is polished.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A prosthesis handling system comprising:
an investment cast metal dental prosthesis structure;
metal handle means attached to said cast metal dental prosthesis structure for handling and supporting said cast metal dental prosthesis structure, said handle having a ball of substantially spherical configuration thereon and a ring on said support means in addition to said ball for engagement by a support for supporting the metal dental prosthesis structure.

2. The prosthesis handling system of claim 1 wherein said ring is attached adjacent said prosthesis and said ball is attached to said ring.

3. The prosthesis handling system of claim 2 wherein said ball is positioned sufficiently away from said ring so that a manually operable instrument having jaws with cavities therein can engage on said ball for handling said prosthesis without covering the opening in said ring.

4. A prosthesis handling system comprising:
a wax master handle for attachment to a wax master prosthesis for investment, said handle having a ball thereon for engagement by ball engaging means for support of the prosthesis; and
a ring on said handle for engagement by a support pin.

5. The prosthesis handling system of claim 4 wherein said ball is mounted on said ring and said ring is mounted on a neck for attachment to the wax master prosthesis.

6. The prosthesis handling system of claim 5 wherein there is a manually operable instrument for engaging said ball, said instrument being shaped so that when said instrument engages said ball said instrument does not overlap the opening in said ring.

* * * * *